US010945928B2

(12) United States Patent
Yamamoto et al.

(10) Patent No.: US 10,945,928 B2
(45) Date of Patent: Mar. 16, 2021

(54) DENTURE BASE COATING COMPOSITION, COATING FILM-BEARING DENTURE BASE, PLATE DENTURE, AND METHOD FOR PRODUCING COATING FILM-BEARING DENTURE BASE

(71) Applicant: FUJIFILM Corporation, Tokyo (JP)

(72) Inventors: Yosuke Yamamoto, Ashigarakami-gun (JP); Akihito Amao, Ashigarakami-gun (JP); Kiyotaka Fukagawa, Ashigarakami-gun (JP); Yuta Shigenoi, Ashigarakami-gun (JP); Natsumi Yokokawa, Ashigarakami-gun (JP); Chiaki Tsutsumi, Tokyo (JP); Noriyuki Wakabayashi, Tokyo (JP); Kazuo Takakuda, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 50 days.

(21) Appl. No.: 16/438,640

(22) Filed: Jun. 12, 2019

(65) Prior Publication Data

US 2019/0290551 A1 Sep. 26, 2019

Related U.S. Application Data

(63) Continuation of application No. PCT/JP2018/002302, filed on Jan. 25, 2018.

(30) Foreign Application Priority Data

Jan. 31, 2017 (JP) ............................ JP2017-015400
Feb. 3, 2017 (JP) ............................ JP2017-018740
Sep. 21, 2017 (JP) ............................ JP2017-181080
Dec. 27, 2017 (JP) ............................ JP2017-250690

(51) Int. Cl.

| | |
|---|---|
| ***A61K 6/083*** | (2006.01) |
| ***A61K 6/887*** | (2020.01) |
| ***A61C 13/36*** | (2006.01) |
| ***A61K 6/00*** | (2020.01) |
| ***A61K 6/72*** | (2020.01) |
| *C08L 33/26* | (2006.01) |
| *A61K 6/35* | (2020.01) |

(52) U.S. Cl.

CPC .......... *A61K 6/887* (2020.01); *A61C 13/1016* (2013.01); *A61K 6/00* (2013.01); *A61K 6/72* (2020.01); *A61K 6/35* (2020.01); *C08L 33/26* (2013.01)

(58) Field of Classification Search

CPC ........................................................ A61K 6/35
See application file for complete search history.

(56) References Cited

U.S. PATENT DOCUMENTS 8,590,999 B2 * 11/2013 Irita ..................... C09D 11/101 347/21
10,385,151 B2 * 8/2019 Fukagawa ............. C08F 220/60
10,456,333 B2 * 10/2019 Nojiri ..................... C09J 133/26
10,736,822 B2 * 8/2020 Amao ..................... A61K 6/887
2004/0122128 A1 6/2004 Nakabayashi et al.
2006/0084717 A1 4/2006 Cohen et al.
2006/0130701 A1 6/2006 Salz et al.
2010/0248190 A1 * 9/2010 Chen ........................ A61K 6/18 433/215
2015/0342838 A1 12/2015 Hara et al.
2017/0226251 A1 8/2017 Fukagawa
2018/0296445 A1 10/2018 Amao et al.

FOREIGN PATENT DOCUMENTS

JP 07187943 A 7/1995
JP 2004-194874 A 7/2004
JP 2006-151850 A1 6/2006
JP 2015-227314 A 12/2015
JP 2016-098202 A 5/2016
JP 2017-002171 A 1/2017
WO 2016/007424 A2 1/2016
WO 2016/067795 A1 5/2016
WO 2016/138528 A1 9/2016
WO 2017/135186 A1 8/2017
WO 2018/212061 A1 11/2018

OTHER PUBLICATIONS

Yan et al., "Hierarchical Polymer Brushes with Dominant Antibacterial Mechanisms Switching from Bactericidal to Bacteria Repellant", BioMacromolecules, vol. 17, No. 5, pp. 1696-1704, Apr. 6, 2016 (9 pages total).
Ginic-Markovic et al., "A versatile approach to grafting biofouling resistant coatings from polymeric membrane surfaces using an adhesive macroinitiator", RSC Advances, vol. 5, No. 77, pp. 63017-63024, Jul. 16, 2015 (8 pages total).
International Search Report dated Apr. 17, 2018 in International Application No. PCT/JP2018/002302.
Written Opinion of the International Searching Authority dated Apr. 17, 2018 in International Application No. PCT/JP2018/002302.
International Preliminary Report on Patentability with translation of Written Opinion dated Aug. 6, 2019 in International Application No. PCT/JP2018/002302.
Hirasawa et al., "Superhydrophilic co-polymer coatings on denture surfaces reduce *Candida albicans* adhesion—An in vitro study", Archives of Oral Biology, 2018: vol. 87, Dec. 27, 2017, pp. 143-150, 8 pages total.
Lazarin et al., "*Candida albicans* adherence to an acrylic resin modified by experimental photopolymerised coatings: an in vitro study", Gerodontology, Jul. 30, 2012, 2014: vol. 31, pp. 25-33, 9 pages total.

(Continued)

*Primary Examiner* — Michael F Pepitone
(74) *Attorney, Agent, or Firm* — Sughrue Mion, PLLC

(57) ABSTRACT

A denture base coating composition includes at least one selected from the group consisting of a first compound represented by Formula (1-0) and a second compound represented by Formula (2-0).

17 Claims, No Drawings

(56) References Cited

OTHER PUBLICATIONS

Extended European Search Report dated Feb. 6, 2020 from European Patent Office in Application No. 18748240.1.
Notice of Reasons for Refusal dated Aug. 11, 2020 from the Japanese Patent Office in Application No. 2018-565492.
Communication dated Oct. 28, 2020, from the European Patent Office in European Application No. 18748240.1.
Pavlinec Juraj et al., "Monomers for adhesive polymers, $8^{a}$ crosslinking polymerization of selected N-substituted bis(acrylamide)s for dental filling materials", Journal of Applied Polymer Science, John Wiley & Sons, Inc, US, vol. 113, No. 5, Sep. 5, 2009 (Sep. 5, 2009), pp. 3137-3145 (9 pages total).

* cited by examiner

DENTURE BASE COATING COMPOSITION, COATING FILM-BEARING DENTURE BASE, PLATE DENTURE, AND METHOD FOR PRODUCING COATING FILM-BEARING DENTURE BASE

CROSS-REFERENCE TO RELATED APPLICATIONS

This application is a Continuation of PCT International Application No. PCT/JP2018/002302, filed on Jan. 25, 2018, which claims priority under 35 U.S.C. § 119(a) to Japanese Patent Application No. 2017-015400, filed on Jan. 31, 2017, Japanese Patent Application No. 2017-018740, filed on Feb. 3, 2017, Japanese Patent Application No. 2017-181080, filed on Sep. 21, 2017, and Japanese Patent Application No. 2017-250690, filed on Dec. 27, 2017. Each of the above application(s) is hereby expressly incorporated by reference, in its entirety, into the present application.

BACKGROUND OF THE INVENTION

1. Field of the Invention

The present invention relates to a denture base coating composition, a coating film-bearing denture base, a plate denture, and a method for producing a coating film-bearing denture base.

2. Description of the Related Art

A plate denture comprising a denture base and artificial teeth formed on the denture base is known. Regarding the material of the denture base, resins having adequate flexibility may be used for the purpose of alleviating the impact on the jaw or the like of a person wearing a plate denture. In JP2016-098202A, a "dental polymerizable composition including a (meth)acrylic polymerizable monomer (a), a hydroperoxide compound (b), a thiourea derivative (c), a transition metal compound (d), a softening agent (e), and a silica powder (f)" is described as a soft material used for the denture base.

SUMMARY OF THE INVENTION

A denture base formed from a (meth)acrylic polymer obtainable by curing the composition including a (meth) acrylic polymerizable monomer as described in JP2016-098202A, has adequate flexibility; however, the inventors of the present invention found that a denture base such as described above has a problem that the denture base is easily scratchable and is likely to have bacteria in the oral cavity adhered to the denture base.

Thus, it is an object of the invention to provide a denture base coating composition that can form a coating film having excellent scratch resistance and an excellent ability to inhibit bacterial attachment on a denture base (hereinafter, also described as "having the effects of the invention").

Furthermore, it is another object of the invention to provide a coating film-bearing denture base, a plate denture, and a method for producing a coating film-bearing denture base.

According to the present specification, scratch resistance and an ability to inhibit bacterial attachment mean physical properties of a coating film (or a denture base itself as a comparison), which is evaluated by the methods described in Examples.

The inventors of the present invention conducted a thorough investigation in order to achieve the objects described above, and as a result, the inventors found that the objects can be achieved by the following configuration.

[1] A denture base coating composition comprising at least one selected from the group consisting of a first compound represented by Formula (1-0) and a second compound represented by Formula (2-0).

[2] The denture base coating composition according to [1], in which the second compound is at least one selected from the group consisting of a compound represented by Formula (2-01) and a compound represented by Formula (2-02).

[3] The denture base coating composition according to [1] or [2], in which the first compound is a compound represented by Formula (1-01), and the second compound is a compound represented by Formula (2).

[4] The denture base coating composition according to any one of [1] to [3], in which the first compound is a compound represented by Formula (1-1) or a compound represented by Formula (1-2), and the second compound is a compound represented by Formula (2-1).

[5] The denture base coating composition according to any one of [1] to [4], in which the coating composition comprises the first compound and the second compound.

[6] The denture base coating composition according to [5], in which a content mass ratio of the content of the first compound to the content of the second compound in the denture base coating composition is 10/90 to 90/10.

[7] The denture base coating composition according to any one of [1] to [6], further comprising a polymerization initiator.

[8] A coating film-bearing denture base comprising a denture base and a coating film formed on the denture base, the coating film being obtained by curing the denture base coating composition according to any one of [1] to [7].

[9] The coating film-bearing denture base according to [8], in which an arithmetic mean roughness Ra of the surface of the denture base on the coating film side is 30 to 1,000 nm.

[10] The coating film-bearing denture base according to [8] or [9], in which the denture base is a surface-treated denture base treated with a surface treating agent.

[11] The coating film-bearing denture base according to [10], in which the surface treating agent includes an organic solvent, and a main component of the organic solvent is at least one selected from the group consisting of a ketone-based solvent, an alcohol-based solvent, an ether-based solvent, and an ester-based solvent.

[12] The coating film-bearing denture base according to [11], in which the main component of the organic solvent is at least one selected from the group consisting of acetone and methyl ethyl ketone.

[13] A plate denture comprising the coating film-bearing denture base according to any one of [8] to [12].

[14] A method for producing a coating film-bearing denture base comprising a denture base and a coating film formed on the denture base, the method comprising: step A of applying the denture base coating composition according to any one of [1] to [7] on the denture base and obtaining a denture base coating composition layer; and step B of applying energy to the denture base coating composition layer, thereby curing the denture base coating composition layer, and obtaining a coating film.

[15] The method for producing a coating film-bearing denture base according to [14], the method further comprising step S of surface-treating the denture base, before the step A.

[16] The method for producing a coating film-bearing denture base according to [15], in which the step S is a step of bringing the surface of the denture base into contact with a surface treating agent.

[17] The method for producing a coating film-bearing denture base according to [16], in which the surface treating agent includes an organic solvent, and a main component of the organic solvent is at least one selected from the group consisting of a ketone-based solvent, an alcohol-based solvent, an ether-based solvent, and an ester-based solvent.

[18] The method for producing a coating film-bearing denture base according to [17], in which the main component of the organic solvent is at least one selected from the group consisting of acetone and methyl ethyl ketone.

According to the invention, a denture base coating composition that can form a coating film having excellent scratch resistance and an excellent ability to inhibit bacterial attachment on a denture base can be provided.

Furthermore, according to the invention, a coating film-bearing denture base, a plate denture, and a method for producing a coating film-bearing denture base can also be provided.

DESCRIPTION OF THE PREFERRED EMBODIMENTS

Hereinafter, the invention will be described in detail.

The explanation of constituent requirements that will be described below may be based on representative exemplary embodiments of the invention, however, the invention is not intended to be limited to those embodiments.

According to the present specification, a value range expressed using the symbol "~" means a range including the values described before and after the symbol "~" as the lower limit and the upper limit.

In regard to the description of a group (atomic group) according to the present specification, a description that does not indicate substitution and unsubstitution includes a group that does not contain a substituent as well as a group that contains a substituent. For example, the term "alkyl group" includes not only an alkyl group that does not contain a substituent (unsubstituted alkyl group) but also an alkyl group that contains a substituent (substituted alkyl group).

The term "actinic rays" or "radiation" according to the present specification means, for example, far-ultraviolet radiation, extreme ultraviolet radiation (EUV), ultraviolet radiation, visible light. X-radiation, and electron beams. Furthermore, the term "light" according to the present specification means actinic rays and radiation. The term "exposure" according to the present specification includes, unless particularly stated otherwise, exposure to far-ultraviolet radiation, ultraviolet radiation, visible light, X-radiation, EUV, and the like, as well as drawing by particle beams such as an electron beam and an ion beam.

According to the present specification, the term "(meth) acrylate" represents acrylate and methacrylate. According to the present specification, the term "(meth)acryl" represents acryl and methacryl. According to the present specification, the term "(meth)acryloyl" represents acryloyl and methacryloyl. Furthermore, according to the present specification, the term "(meth)acrylamide" represents acrylamide and methacrylamide.

[Denture Base Coating Composition]

The denture base coating composition according to an embodiment of the invention includes at least one selected from the group consisting of a first compound represented by Formula (1-0) that will be described below, and a second compound represented by Formula (2-0) that will be described below.

The mechanism by which the denture base coating composition according to the embodiment has the effects of the invention is not necessarily clear; however, a mechanism that is speculated by the present inventors will be described below. However, the invention is not limited such that the effects of the invention can be obtained by the following mechanism. In other words, even a case in which the effects of the invention are obtained by a mechanism other than the mechanism described below, is also included in the scope of the invention.

In a case in which a denture base is formed from a soft material such as a (meth)acrylic polymer, the denture base may be damaged by brushing or the like. It is speculated that when the denture base is damaged, in addition to impairment of the esthetic appearance, the denture base is brought to a state in which bacteria in the oral cavity are further proliferated and become more easily attachable by the concavities and convexities formed on the surface of the denture base. It is contemplated that in a case in which bacteria adhere to the denture base, the bacteria cause inflammation in the oral cavity of the person who uses a plate denture, and cause foul breath in the person who uses a plate denture.

Furthermore, since (meth)acrylic polymers are hydrophobic, it is speculated that bacteria in the oral cavity, particularly *candida* bacteria (for example, *C. albicans*), caries-causing bacteria (for example, *Streptococcus mutans, Streptococcus sobrinus, Lactobacillus*, and *Actinomyces naeslundii*), periodontal disease bacteria (for example, *Porphyromonas gingivalis, Tannerella forsythensis, Treponema denticola, Prevotella intermedia, Actinobacillus actinomvcetemcomitans, Aggregatibacter actinomycetemcomitans*, and *Fusobacterium nucleatum*), and the like may adhere more easily.

The denture base coating composition according to the above-described embodiment comprises a first compound represented by Formula (1-0) and/or a second compound represented by Formula (2-0). Since the above-described compounds can form a more smooth and strong coating film, it is speculated that a denture base (coating film-bearing denture base) including a coating film formed from the denture base coating composition described above has excellent scratch resistance. Furthermore, it is speculated that in addition to the fact that the surface of the coating film is smooth, since the coating film acquires hydrophilicity by the action of the first compound and/or the second compound, bacteria in the oral cavity, particularly *Candida* bacteria, caries-causing bacteria (for example, *Streptococcus mutans, Streptococcus sobrinus, Lactobacillus*, and *Actinomyces naeslundit*), and periodontal disease bacteria (for example, *Porphromonas gingivalis, Tannerella forsythensis, Treponema denticola, Prevotella intermedia, Actinobacillus actinomycetemcomitans. Aggregatibacter actinomycetemcomitans*, and *Fusobacterium nucleatum*), and the like may not easily adhere to the denture base. Therefore, it is speculated that the coating film-bearing denture base has an excellent ability to inhibit bacterial attachment.

In the following description, the various components included in the denture base coating composition according to the above-described embodiment will be explained.

[First Compound]

The first compound is a compound represented by Formula (1-0). The content of the first compound in the denture base coating composition is not particularly limited; however, generally, the content is preferably 0.01% by mass or more, more preferably 1% by mass or more, even more preferably 10% by mass or more, and particularly preferably 20% by mass or more, with respect to the total solid content of the denture base coating composition. The upper limit is preferably 99% by mass or less, more preferably 90% by mass or less, and even more preferably 80% by mass or less. Regarding the first compound, one kind thereof may be used alone, or two or more kinds thereof may be used in combination. In a case in which two or more kinds of the first compound are used in combination, it is preferable that the total content is within the range described above.

In a case in which the denture base coating composition comprises the first compound and a second compound that will be described below, the content mass ratio of the content of the first compound to the content of the second compound that will be described below in the denture base coating composition is not particularly limited; however, generally, the content mass ratio is preferably 0.1/99.9 to 99.9/0.1. From the viewpoint of obtaining a denture base coating composition that exhibits superior effects of the invention, the content mass ratio is more preferably 10/90 to 90/10.

(1-0)

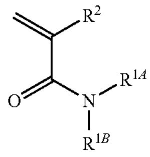

In Formula (1-0), $R^{1A}$ and $R^{1B}$ each independently represent a group represented by Formula (1A) or a hydrogen atom, at least one selected from the group consisting of $R^{1A}$ and $R^{1B}$ is a group represented by Formula (1A), and it is preferable that one of $R^{1A}$ or $R^{1B}$ is a group represented by Formula (1A).

In Formula (1-0), $R^2$ represents a hydrogen atom or a methyl group, and a methyl group is more preferred.

(1A)

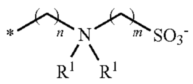

In Formula (1A), $R^1$'s each independently represent a methyl group, an ethyl group, an n-propyl group, or an i-propyl group, m represents an integer from 1 to 4, and is preferably 3 or 4. n represents an integer from 2 to 4, and is preferably 3 or 4, and more preferably 3. A plurality of $R^1$'s may be identical with or different from one another.

In Formula (1A), the symbol * represents the position of linkage to the nitrogen atom in Formula (1-0).

Specific examples of the compound represented by Formula (1-0) include, for example, the compounds described in paragraph 0022 of WO2016/067795A, the disclosure of which is incorporated herein by reference.

The C Log P value of the first compound represented by Formula (1-0) is not particularly limited; however, from the viewpoint that a coating film thus obtainable acquires superior hydrophilicity, and consequently, the coating film acquires a superior ability to inhibit bacterial attachment, the upper limit is preferably less than −7.2, more preferably −7.5 or less, more preferably −7.8 or less, more preferably −8.0 or less, more preferably −8.2 or less, more preferably −8.5 or less, more preferably −8.7 or less, and most preferably −9.0 or less. The lower limit of C Log P value of the first compound represented by Formula (1) is not particularly limited; however, the lower limit is generally preferably −20 or greater, more preferably −12 or greater, and even more preferably −10 or greater.

According to the present specification, the C Log P value means the "C Log P value" calculated using Chem Bio Craw Ultra ver. 12.0 (CambridgeSoft Corporation, USA).

Here, the C Log P value is a value estimating the Log P value, which is a coefficient representing the affinity of an organic compound to water and 1-octanol, by calculation. The 1-octanol/water partition coefficient P is the ratio of equilibrium concentrations of a compound in a partition equilibrium achieved in a case in which a trace amount of the compound is dissolved as a solute in a solvent of two liquid phases of 1-octanol and water, the equilibrium concentrations of the compound being concentrations of the compound in the respective solvents, and the Log P value is a value expressed as the logarithm Log P on the basis of 10. That is, the "Log P value" is a logarithmic value of the partition coefficient of 1-octanol/water and is known as a parameter representing the hydrophilicity and hydrophobicity of a molecule.

Specific examples of the first compound represented by Formula (1-0) are shown in Table 1. However, the first compound represented by Formula (1-0) is not limited to these. The C Log P values in Table 1 are values calculated by the method described above.

TABLE 1

| Compound represented by Formula (1-0) | CLogP value |
|---|---|
| 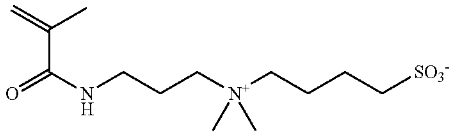 | −9.5 |
| 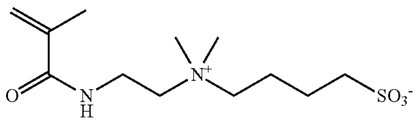 | −8.6 |

TABLE 1-continued

| Compound represented by Formula (1-0) | CLogP value |
|---|---|
| 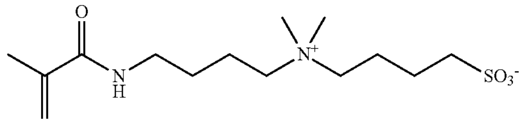 | −10.9 |
| 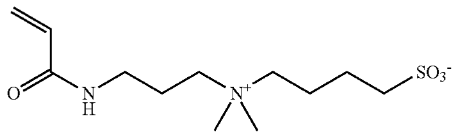 | −9.8 |
| 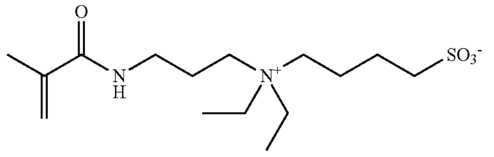 | −8.5 |
| 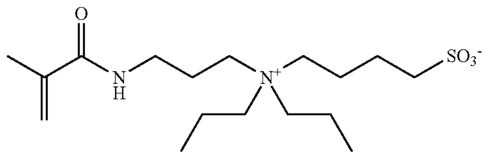 | −7.4 |
| 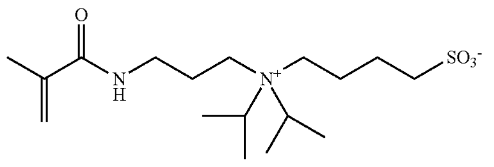 | −7.8 |

Among them, from the viewpoint that a denture base coating composition exhibiting superior effects of the invention is obtained, the first compound is more preferably a compound represented by Formula (1-01).

(1-01)

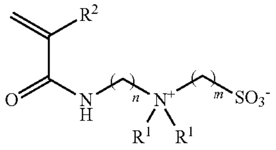

In Formula (1-01), $R^1$'s each independently represent a methyl group, an ethyl group, an n-propyl group, or an i-propyl group, $R^2$ represents a hydrogen atom or a methyl group, and m represents an integer from 1 to 4, and is preferably 3 or 4. n represents an integer from 2 to 4, and is preferably 3 or 4, and more preferably 3. Meanwhile, a plurality of $R^1$'s may be identical with or different from one another.

Among them, from the viewpoint that a denture base coating composition exhibiting superior effects of the invention is obtained, the first compound is more preferably a compound represented by Formula (1-1) or a compound represented by Formula (1-2).

(1-1)

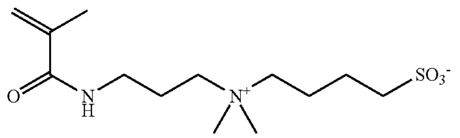

(1-2)

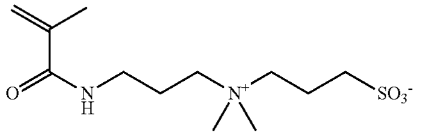

The method for producing the first compound is not particularly limited, and any known method can be used. Regarding the method for producing the first compound, for example, the Synthesis Examples and/or exemplary compounds described in JP2012-187907A. JP2012-031400A, and the like can be referred to. Specifically, a polyamine compound is reacted with a (meth)acrylic acid chloride compound, and thereby a (meth)acrylamide compound containing an amino group is obtained. This is reacted with a sultone compound having a predetermined number of carbon atoms, and thus a first compound can be obtained. Specifically, the production method described in paragraphs 0189 to 0193 of JP2012-031400A can be used, the disclosure of which is incorporated herein by reference.

[Second Compound]

The second compound is a compound represented by Formula (2-0). The content of the second compound in the denture base coating composition is not particularly limited; however, generally, the content is preferably 0.01% by mass or more, more preferably 1% by mass or more, and even more preferably 20% by mass or more, with respect to the total solid content of the denture base coating composition. The upper limit is preferably 99% by mass or less, more preferably 90% by mass or less, and even more preferably 80% by mass or less. Regarding the second compound, one kind thereof may be used alone, or two or more kinds thereof may be used in combination. In a case in which two or more kinds of the second compound are used in combination, it is preferable that the total content is within the range described above.

(2-0)

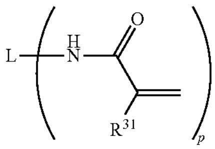

In Formula (2-0), $R^{31}$ represents a hydrogen atom or a methyl group; p represents an integer from 2 to 4, L represents a p-valent linking group, and a plurality of $R^{31}$'s may be identical with or different from one another.

The p-valent linking group for L is not particularly limited. In a case in which L is a divalent linking group, examples include a divalent aliphatic hydrocarbon group, a divalent aromatic hydrocarbon group, —O—, —S—, —N(Rx)- (Rx: a monovalent organic group), —C(=O)—, —C(=O)—O—, —O—C(=O)—O—, —C(=O)—NH—, —O—C(=O)—NH—, —S(=O)—, —S(=O)—O—, $—S(=O)_2—$, —S(=O)—O—, —CH=N—, and groups combining these (for example, an alkyleneoxy group, an alkyleneoxycarbonyl group, and an alkylenecarbonyloxy group).

In a case in which L represents a trivalent or tetravalent linking group, examples include trivalent linking groups such as a trimethylolpropane residue, and an isocyanuric ring containing three units of $—(CH_2)_k—$ (here, k represents, for example, an integer from 2 to 6); and tetravalent linking groups such as a pentaerythritol residue.

Furthermore, L may be a group represented by any one of Formulae (K) to (O), or may be a group in which a hydrogen atom is bonded to one or more of the position of bonding represented by the symbol * in each of the formulae.

(K)

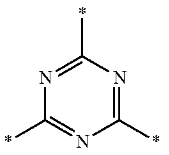

(L)

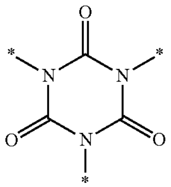

-continued (M)

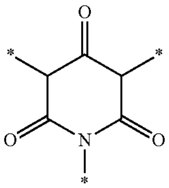

(N)

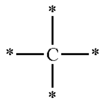

(O)

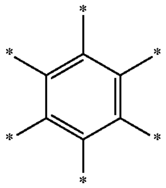

L may also be a group represented by the following formula. The symbol * represents a position of bonding.

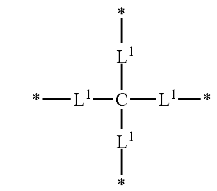

In the above formula, $L^1$'s each independently represent a single bond or a divalent linking group, and a plurality of $L^1$'s may be identical with or different from one another.

$R^{31}$ is preferably a hydrogen atom.

A suitable form of the second compound may be a compound represented by Formula (2-01) or a compound represented by Formula (2-02).

(2-01)

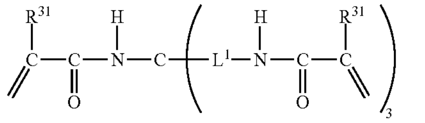

(2-02)

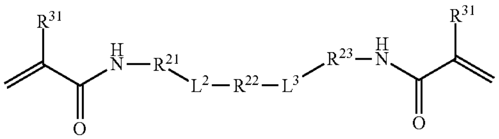

(III)

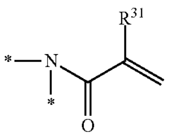

In Formula (2-01), $R^{31}$'s each independently represent a hydrogen atom or a methyl group, and $L^1$'s each independently represent —O—, an alkylene group having 2 to 4 carbon atoms, or a divalent linking group combining these.

In Formula (2-02), $R^{31}$'s each independently represent a hydrogen atom or a methyl group. $R^{21}$ and $R^{23}$ each independently represent —O—, an alkylene group having 1 to 4 carbon atoms, or a divalent linking group combining these, $R^{22}$ represents —O—, an alkylene group having 1 to 4 carbon atoms, a group represented by Formula (III), or a divalent linking group combining these, and $L^2$ and $L^3$ each independently represent a single bond or a group represented by Formula (III).

In Formula (III), $R^{31}$ represents a hydrogen atom or a methyl group, and the symbol * represents a position of bonding.

It is preferable that a carbon atom is positioned at the position adjacent to the nitrogen atom in the amide group adjacent to $R^{21}$ and $R^{23}$. The group adjacent to the nitrogen atom in the amide group is preferably an alkylene group having 1 to 4 carbon atoms.

Examples of the "divalent linking group combining these" include alkylene groups having 1 to 4 carbon atoms and containing —O—, such as $—OCH_2—$, $—OCH_2CH_2—$, $—OCH_2CH_2CH_2—$, $—OCH_2CH_2CH_2CH_2—$, $—CH_2OCH_2—$, $—CH_2OCH_2CH_2—$, and $—CH_2OCH_2CH_2CH_2—$; and a group represented by the formula: —(O-alkylene group (having 1 to 4 carbon atoms))$_n$- (here, n represents an integer of 2 or greater. The upper limit is not particularly limited; however, the upper limit is generally preferably 100) or less).

For the respective groups listed as examples of the "divalent linking group combining these", any one of two bonding sites may be bonded to the amide group.

Above all, from the viewpoint that a denture base coating composition exhibiting superior effects of the invention is obtained, it is more preferable that $R^{21}$ and $R^{23}$ each represent an alkylene group having 1 to 4 carbon atoms, a group combining —O— and an alkylene group having 1 to 4 carbon atoms.

$R^{22}$ represents —O—, an alkylene group having 1 to 4 carbon atoms, a group represented by Formula (III), or a divalent linking group combining these.

Examples of the "divalent linking group combining these" include the groups described above as $R^{21}$ and $R^{23}$. Meanwhile, in a case in which a group represented by Formula (III) is combined with another group, it is preferable that an alkylene group having 1 to 4 carbon atoms is bonded to the nitrogen atom in the group represented by Formula (111).

Among them, from the viewpoint that a denture base coating composition exhibiting superior effects of the invention is obtained, $R^{22}$ is preferably an alkylene group having 1 to 4 carbon atoms, a group combining —O— and an alkylene group having 1 to 4 carbon atoms, or a group represented by Formula (111).

$L^2$ and $L^3$ each independently represent a single bond or a group represented by Formula (III). In a case in which $R^{22}$ represents a group represented by Formula (III), it is preferable that $L^2$ and $L^3$ are both single bonds.

$R^{31}$ is preferably a hydrogen atom.

In General Formula (III), usually, a carbon atom is positioned at the site of the symbol *.

Specific examples of the compound represented by Formula (2-01) or the compound represented by Formula (2-02) are shown below.

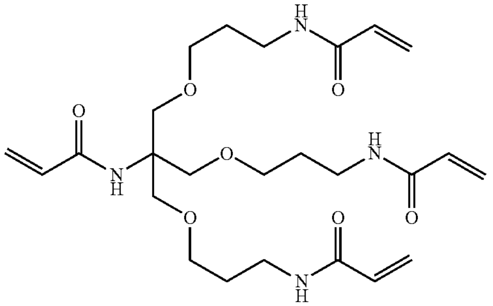

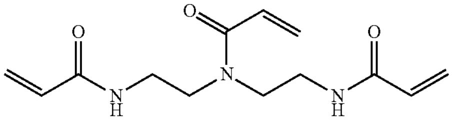

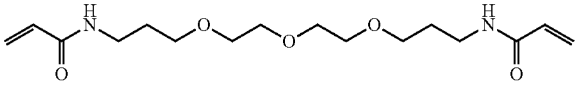

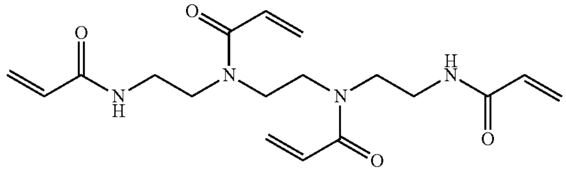

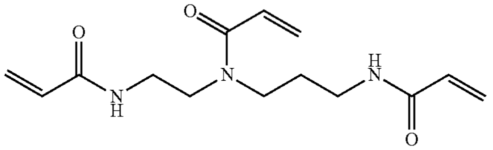

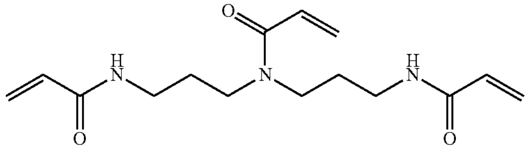

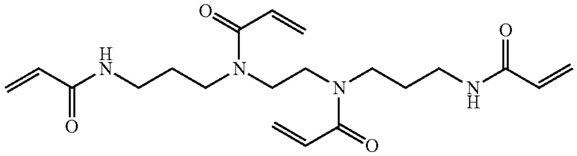

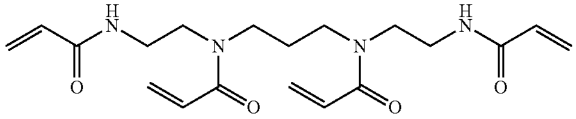

It is preferable that the second compound is a compound represented by Formula (2).

(2)

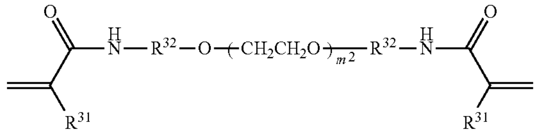

In Formula (2), $R^{31}$'s each independently represent a hydrogen atom or a methyl group, and is preferably a hydrogen atom.

$R^{32}$'s each independently represent an ethylene group, a 1,2-propylene group, or a 1,3-propylene group, and is preferably a 1,3-propylene group.

$m^2$ represents an integer from 0 to 2, and is preferably 1 or 2, and more preferably 2.

A plurality of $R^{31}$'s and a plurality of $R^{32}$'s may be identical with or different from one another, and it is preferable that they are identical with one another.

Above all, from the viewpoint that a denture base coating composition exhibiting superior effects of the invention is obtained, the second compound is preferably a compound represented by Formula (2-1).

(2-1)

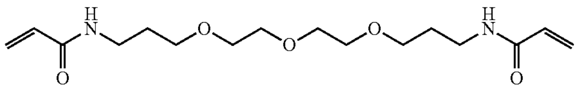

The method for producing the second compound is not particularly limited, and any known production method can be used. Regarding the method for producing the second compound, for example, the method described in paragraphs 0031 to 0033 of JP2013-194023 may be mentioned, the disclosure of which is incorporated herein by reference.

<Suitable Embodiment of Denture Base Coating Composition>

It is preferable that the denture base coating composition comprises the first compound and the second compound, from the viewpoint of exhibiting superior effects of the invention. Above all, from the viewpoint of exhibiting even superior effects of the invention, it is more preferable that the denture base coating composition comprises a first compound represented by formula (1-1) or Formula (1-2) and a second compound represented by Formula (2-1). A suitable embodiment of the content mass ratio of the content of the first compound to the content of the second compound in the denture base coating composition according to the above-described suitable embodiment is as explained above.

Furthermore, regarding the denture base coating composition, from the viewpoint that the composition exhibits superior effects of the invention, it is preferable that the monomer and polymer to be included comprise at least one selected from the group consisting of the first compound and the second compound.

[Optional Components]

The denture base coating composition according to embodiments of the invention may include optional components other than those described above, to the extent that the effects of the invention are obtained. Examples of the optional components include a solvent, a polymerization initiator, a chain transfer agent, a polymerizable monomer (provided that the first compound and the second compound are excluded), a filler, a silane coupling agent, a polymerization inhibitor, a fragrance, a colorant, an algefacient, a preservative, an antibacterial agent, a sensitizer, a reducing agent, and a surfactant. For all of these, known compounds can be used.

<Solvent>

It is preferable that the denture base coating composition includes a solvent. The content of the solvent in the denture base coating composition is not particularly limited; however, it is preferable to adjust the solid content of the denture base coating composition to be 0.1% to 100% by mass, more preferably to 1% to 60% by mass, and even more preferably to 3% to 40% by mass. Regarding the solvent, one kind thereof may be used alone, or two or more kinds thereof may be used in combination. In a case in which two or more kinds of solvents are used in combination, it is preferable that the total content is within the range described above.

The solvent is not particularly limited, and any known solvent can be used. Regarding the solvent, for example, water or an organic solvent may be used.

The organic solvent is not particularly limited, and any known organic solvent can be used. Examples of the organic solvent include alcohols such as methanol, ethanol, and isopropyl alcohol; ethers such as ethylene glycol dimethyl ether and diethylene glycol dimethyl ether; cyclic ethers such as oxysilane, tetrahydrofuran, and 1,4-dioxane; ketones such as acetone and methyl ethyl ketone; chlorinated hydrocarbons such as methylene chloride and chloroform; acetonitrile, and dimethylformamide. Among them, alcohols are preferred, and methanol and ethanol are more preferred.

<Polymerization Initiator>

It is preferable that the denture base coating composition includes a polymerization initiator.

The polymerization initiator is not particularly limited, and any known polymerization initiator can be used. The content of the polymerization initiator in the denture base coating composition is not particularly limited; however, generally, the content is preferably 0.01% to 50% by mass, more preferably 0.05% to 30% by mass, and even more preferably 0.1% to 20% by mass, with respect to the total solid content of the denture base coating composition. Regarding the polymerization initiator, one kind thereof may be used alone, or two or more kinds thereof may be used in combination. In a case in which two or more kinds of polymerization initiators are used in combination, it is preferable that the total content is within the range described above.

Examples of the polymerization initiator include a thermal polymerization initiator and a photopolymerization initiator. Examples of the polymerization initiator include an organohalogen compound, an oxydiazole compound, a carbonyl compound, a diketone compound (for example, camphor-quinone), a ketal compound, a benzoin compound, an acridine compound, an organic peroxide, an azo compound, a coumarin compound, an azide compound, a metallocene compound, a hexaarylbiimidazole compound, an organic boric acid compound (for example, TBB (tri-n-butylborane)), a disulfonic acid compound, an oxime compound, an onium salt compound (for example, diphenyliodonium hexafluorophosphate), a hydroxyalkylphenone compound, an aminoalkylphenone compound, and an acylphosphine compound (for example, 2,4,6-trimethylbenzoyl-diphenylphosphine oxide or bis(2,4,6-trimethylbenzoyl)-phenylphoshine oxide).

Furthermore, an initiator that generates a radical by an oxidation-reduction reaction without using heat or light may also be used. Examples of such an initiator include a combination of a peroxide (for example, benzoyl peroxide) and an amine compound (N,N-dimethylaniline or the like).

The polymerization initiator may be used in combination with a sensitizer and/or a reducing agent.

Regarding the polymerization initiator, the description of paragraph 0135 and thereafter of JP2010-106268A (paragraph 0163 and thereafter of corresponding US Patent App. No. 2011/0124824), and the description of paragraphs 0018 to 0025 of JP2009-013115A, and the description of paragraphs 0018 to 0025 of JP2005-154312A can be referred to, the disclosures of which are incorporated herein by reference.

Regarding the sensitizer, the description of paragraph 154 of WO2017/086224A and the description of paragraph 0024 of JP2005-154312A can be referred to, the disclosures of which are incorporated herein by reference.

Regarding the reducing agent, a tertiary amine compound or a mercapto compound is generally used. Examples of the tertiary amine compound include methyl 4-N,N-dimethylaminobenzoate, ethyl 4-N,N-dimethylaminobenzoate, and 4-N,N-dimethylaminobenzonitrile. Examples of the mercapto compound include 2-mercaptobenzothiazole, 2-mercaptobenzoxazole, and 2-mercaptobenzimidazole. Furthermore, the description of paragraph 0025 of JP2005-154312A can be referred to, the disclosure of which is incorporated herein by reference.

Regarding the polymerization initiator, one kind thereof may be used alone, or two or more kinds thereof may be used in combination.

<Polymerizable Monomer>

The denture base coating composition may further include a polymerizable monomer, from the viewpoint that a coating film thus obtainable has superior adhesiveness to the denture base. The polymerizable monomer according to the present specification means a compound that contains at least one polymerizable group in the molecule and is different from any of the first compound and the second compound.

The content of the polymerizable monomer in the denture base coating composition is not particularly limited; however, generally, the content is preferably 0.01% to 90% by mass, more preferably 20% to 80% by mass, and even more preferably 30% to 70% by mass, with respect to the total solid content of the denture base coating composition. Regarding the polymerizable monomer, one kind thereof may be used alone, or two or more kinds thereof may be used in combination. In a case in which two or more kinds of polymerizable monomers are used in combination, it is preferable that the total content is within the range described above.

The polymerizable monomer may be any monomer used in the field of dentistry, and examples include an aliphatic monofunctional polymerizable monomer, an aliphatic bifunctional polymerizable monomer, an aliphatic trifunctional or higher-functional polymerizable monomer, and an aromatic monofunctional polymerizable monomer.

Examples of the aliphatic monofunctional polymerizable monomer include methyl (meth)acrylate, ethyl (meth)acrylate, propyl (meth)acrylate, butyl (meth)acrylate, isobutyl (meth)acrylate, lauryl (meth)acrylate, and 2-hydroxyethyl (meth)acrylate.

Examples of the aliphatic bifunctional polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, butylene glycol di(meth)acrylate, and 2,2,4-trimethylhexamethylenebis(2-carbamoyloxyethyl) dimethcrylate.

Examples of the aliphatic trifunctional or higher-functional polymerizable monomer include trimethylolpropane tri(meth)acrylate, trimethylolethane tri(meth)acrylate, trimethylolmethane tri(meth)acrylate, ethoxylated isocyanuric acid tri(meth)acrylate, pentaerythritol tri(meth)acrylate, pentaerythritol tetra(meth)acrylate, dipentaerythritol tri (meth)acrylate, dipentaerythritol tetra(meth)acrylate, dipentaerythritol penta(meth)acrylate, and dipentaerythritol hexa (meth)acrylate.

Examples of the aromatic monofunctional polymerizable monomer include benzyl (meth)acrylate, phenoxyethyl (meth)acrylate, and phenoxydiethylene glycol (meth)acrylate. Examples of an aromatic bifunctional polymerizable monomer include 2,2-bis[4-[2-hydroxy-3-(methacryloyloxy)propyloxy]phenyl]propane.

As a polymerizable monomer other than those, the hydrophobic monomers described in paragraphs 0035 to 0039 of JP2006-151850A can also be used, the disclosure of which is incorporated herein by reference.

Furthermore, the description of paragraphs 0018 to 0022 of JP2005-154312A can be referred to, the disclosure of which is incorporated herein by reference.

As a polymerizable monomer other than those, any known polyfunctional acrylamide monomer (N,N'-ethylenebisacrylamide, N,N'-(1,2-dihydroxyethylene)bisacrylamide, 1,3,5-triacryloylohexahydro-1,3,5-triazine, or the like) or monofunctional acrylamide monomer (N,N-dimethylacrylamide, 4-acryloylomorpholine, or the like) can also be used.

As a polymerizable monomer other than those, a betaine monomer (N-methacryloyloxyethyl-N,N-dimethylammoniummethyl-α-carboxybetaine, or 2-methacryloyloxyethylphosphorylcholine), a cationic monomer (2-(acryloylamino)-N,N,N-trimethylethaneammonium chloride or the like), an anionic monomer (sodium 2-acrylamido-2-methylpropanesulfonate or the like), a monomer containing an alkylpyridinium salt (methacryloyloxydodecylpyridinium bromide), or the like, all of which are known, can also be used.

<Filler>

The denture base coating composition may include a filler. A coating film obtainable using a denture base coating composition including a filler has superior mechanical strength and superior adhesiveness to the denture base. The content of the filler in the denture base coating composition is not particularly limited; however, generally, the content is preferably 0.01% to 80% by mass, more preferably 0.05% to 50% by mass, and even more preferably 0.1% to 30% by mass, with respect to the total solid content of the denture base coating composition. Regarding the filler, one kind thereof may be used alone, or two or more kinds thereof may be used in combination. In a case in which two or more kinds of fillers are used in combination, it is preferable that the total content is within the range described above.

The average particle size of the filler is not particularly limited; however, generally, the average particle size is preferably 0.01 to 500 μm, more preferably 0.05 to 100 μm, and even more preferably 0.1 to 50 μm. The average particle size of a filler according to the present specification means an average particle size measured by a Coulter method.

Examples of the filler include an organic filler, an inorganic filler, and a composite filler of these.

Examples of the organic filler include poly(methyl methacrylate), poly(ethyl methacrylate), a methyl methacrylate-ethyl methacrylate copolymer, a crosslinked type poly(methyl methacrylate), a crosslinked type poly(ethyl methacrylate), a polyester, a polyamide, a polycarbonate, polyphenylene ether, polyoxymethylene, polyvinyl chloride, polystyrene, polyethylene, polypropylene, an ethylene-vinyl acetate copolymer, and an acrylonitrile-styrene copolymer.

Examples of the inorganic filler include lanthanide glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass.

The inorganic filler may be used after being surface-treated in advance with a known surface treating agent such as a silane coupling agent, in order to adjust the miscibility with other components such as the first compound and the second compound.

Examples of the surface treating agent include vinyltrimethoxysilane, vinyltriethoxysilane, vinyltrichlorosilane, vinyltri(β-methoxyethoxy)silane, 3-methacryloyloxypropyltrimethoxysilane, 11-methacryloyloxyundecyltrimethoxysilane, 3-glycidoxypropyltrimethoxysilane, 3-mercaptopropyltrimethoxysilane, and 3-aminopropyltriethoxysilane. Regarding the surface treating agent, one kind thereof may be used alone, or two or more kinds thereof may be used in combination.

The composite filler is not particularly limited; however, for example, a composite filler obtainable by adding a monomer to the above-described inorganic filler in advance, processing the mixture into a paste form, subsequently polymerizing the monomer, and pulverizing the resultant, may be mentioned. Examples of the composite filler include a TMPT filler (a product obtained by mixing trimethylolpropane methacrylate and a silica filler, polymerizing the mixture, and then pulverizing the resultant), and inorganic microparticles that have been surface-modified with an alkoxysilane having an unsaturated double bond as described in JP2005-154312A.

<Silane Coupling Agent>

The denture base coating composition may further include a silane coupling agent.

The content of the silane coupling agent in the denture base coating composition is not particularly limited; however, generally, the content is preferably 0.01% to 50% by mass, more preferably 0.05% to 30% by mass, and even more preferably 0.1% to 20% by mass, with respect to the total solid content of the denture base coating composition. Regarding the silane coupling agent, one kind thereof may be used alone, or two or more kinds thereof may be used in combination. In a case in which two or more kinds of silane coupling agents are used in combination, it is preferable that the total content is within the range described above.

The silane coupling agent is not particularly limited, and any known silane coupling agent can be used. Examples of the silane coupling agent include the silane coupling agents described in paragraph 0058 of JP2015-214514A, the disclosure of which is incorporated herein by reference.

<Other Additives>

The denture base coating composition may further include other additives, for the purpose of regulating the intermolecular interaction between the various components constituting the denture base coating composition and the intermolecular interaction between a coating film obtainable using the denture base coating composition and the denture base interface.

Examples of the other additives include a phenolic compound, a polymer obtainable by polymerizing an aliphatic monofunctional polymerizable monomer, a hydrophilic elastomer, and an azide compound. The other additives may be incorporated into the denture base coating composition so that the denture base coating composition can form a uniform coating film. Furthermore, in a case in which the denture base coating composition does not include the other additives, the other additives may be disposed in a film form as an undercoat of the coating film, between the coating film and the denture base interface.

Among the phenolic compounds, from the viewpoint that a strong intermolecular interaction is enabled by multi-point hydrogen bonding, compounds containing a catechol group, a pyrogallol group, and the like as a partial structure are preferred. Examples of the catechol group include the partial structures described in JP2014-101475A.

It is also preferable that the phenolic compound is used as a polymerizable monomer or a polymer, from the viewpoint of compatibility with other components.

Examples of a polymer obtainable by polymerizing an aliphatic monofunctional polymerizable monomer include HEMA (hexaethyl methacrylate), glycerol dimethacrylate, and copolymers of hydrophilic compounds such as the first compound and the second compound with the aliphatic monofunctional polymerizable monomers described above.

It is preferable that the type of the aliphatic monofunctional polymerizable monomer is adjusted as appropriate by taking the compatibility with the denture base coating composition and/or the polarity of the base material into consideration.

Examples of a hydrophilic elastomer include a hydrocarbon-based elastomer containing a carboxylic acid group or a carboxylic acid salt group, a polyurethane elastomer, and the elastomers described in JP4401262B.

Examples of the azide compound include the compounds described in JP2010-059367A.

[Coating Film-Bearing Denture Base]

The coating film-bearing denture base according to embodiments of the invention comprises a denture base and a coating film formed on the denture base by curing the denture base coating composition described above.

The denture base is not particularly limited, and any known denture base can be used.

The material for the denture base is not particularly limited; however, a resin is preferred. The type of the resin is not particularly limited; however, it is more preferable that the material includes a (meth)acrylic polymer having superior adaptability to the living body.

Regarding the material for the denture base, for example, a resin obtained by curing the dental polymerizable composition described in paragraphs 0011 to 0079 of JP2016-098202A, and the materials described in paragraph 0072 of JP2017-042394A, the disclosures of which are incorporated herein by reference.

The denture base used for the coating film-bearing denture base according to the embodiments of the invention may be a primer layer-bearing denture base having a denture base and a primer layer disposed so as to coat at least a portion of the denture base. In a case in which a primer layer-bearing denture base is used, the adhesiveness between the coating film and the denture base can be further increased.

The primer layer is not particularly limited, and a layer formed using any known composition for forming a dental primer layer can be used. Main components of a composition for forming a primer layer include a monomer having a silane coupling group, and monomers including a carboxylic acid monomer, a phosphoric acid monomer (also including a phosphoric acid ester monomer), and an acrylic acid ester monomer.

Furthermore, the denture base used for the coating film-bearing denture base according to the embodiments of the invention may be a surface-treated denture base that has been subjected to a surface treatment. In a case in which a surface-treated denture base is used, the adhesiveness between the coating film and the denture base can be further increased.

The method for the surface treatment is not particularly limited; however, typically, a surface treatment method capable of forming concavities and convexities that will be described below on the surface of a denture base (surface roughening treatment) is preferred. Examples of such a surface treatment method include a sand blast method, a method of polishing with a polishing paper, a surface roughening treatment of using a treating agent method, and the like.

A treating agent method is a method of roughening the surface of a denture base by bringing the denture base into contact with a surface treating agent. The method of bringing the surface of a denture base into contact with a surface treating agent is not particularly limited; however, examples include a method of immersing a denture base in a surface treating agent, a method of applying a surface treating agent on a denture base, and a method of spraying a surface treating agent onto a denture base.

It is preferable that the surface treating agent includes an organic solvent. The organic solvent included in the surface treating agent is not particularly limited; however, examples include a halogen-based solvent, a ketone-based solvent, an alcohol-based solvent, an ether-based solvent, and an ester-based solvent.

The content of the organic solvent in the surface treating agent is not particularly limited; however, the content is preferably 20% to 100% by mass with respect to the total mass of the organic solvent.

Regarding the organic solvent, one kind thereof may be used alone, or two or more kinds thereof may be used in combination. In a case in which two or more kinds of organic solvents are used in combination, it is preferable that the total content is within the range described above.

Among them, from the viewpoint that the concavities and convexities that will be described below can be easily formed on the surface of the denture base, the main component of the organic solvent included in the surface treating agent is preferably at least one selected from the group consisting of a ketone-based solvent, an alcohol-based solvent, an ether-based solvent, and an ester-based solvent; and more preferably at least one selected from the group consisting of acetone and methyl ethyl ketone.

According to the present specification, the main component means, in a case in which one kind of organic solvent is included in the surface treating agent, the aforementioned one kind of organic solvent, and in a case in which two or more kinds of organic solvents are included in the surface treating agent, the main component means the organic solvent of the largest content among the two or more kinds of organic solvents.

In a case in which two or more kinds of organic solvents of the largest content are included in the surface treating agent, the aforementioned two or more kinds of organic solvents are respectively considered as main components.

The surface treating agent may include components other than the organic solvent. Examples include polymers that are conventionally used as a component of a dental surface treating agent, and known polymers.

A surface-treated denture base that has been subjected to the above-described surface roughening treatment has, in a case in which a coating film is provided on the surface of the denture base, superior interlayer adhesiveness between the denture base and the coating film.

The arithmetic mean roughness Ra of the surface of the denture base on the coating film side in a coating film-bearing denture base is not particularly limited; however, the arithmetic mean roughness Ra is generally preferably 10 to 1,200 nm, more preferably 30 nm to 1,000 nm, even more preferably 50 nm to 800 nm, and particularly preferably 100 nm to 500 nm.

The arithmetic mean roughness Ra can be measured by observing the surface of a surface-treated denture base before being provided with a coating film, by means of a contact needle method and a non-contact type interference microscope.

Regarding other surface treatment methods, for example, a corona discharge treatment, a chromic acid treatment, a flame treatment, a hot air treatment, an ozone treatment, a plasma treatment, an ultraviolet irradiation treatment, a surface oxidation treatment, and the like can also be used.

The thickness of the coating film formed on the denture base is not particularly limited; however, generally, the thickness is preferably 0.1 to 500 μm, more preferably 0.5 to 100 μm, and even more preferably 1 to 50 μm.

The method for producing the coating film-bearing denture base according to the above-described embodiment is not particularly limited, and any known production method can be used. Above all, from the viewpoint that a coating film-bearing denture base is obtained more conveniently, it is preferable that the coating film-bearing denture base is produced by the method that will be described below.

[Plate Denture]

A plate denture according to the embodiments of the invention comprises the above-described coating film-bearing denture base and artificial teeth. The plate denture may be a full denture or may be a partial denture. Furthermore, the artificial teeth are not particularly limited, and any known artificial teeth can be used. The method for producing a plate denture is not particularly limited, and any known production method can be used.

[Method for Producing Coating Film-Bearing Denture]

A method for producing a coating film-bearing denture base according to the embodiments of the invention comprises the following steps. According to a method for producing a coating film-bearing denture base including the following steps, a coating film-bearing denture base can be produced more conveniently.

(1) Step A of applying a denture base coating composition on a denture base and thereby obtaining a coating composition layer.

(2) Step B of applying energy to the denture base coating composition layer, thereby curing the denture base coating composition layer, and obtaining a coating film.

In the following description, the respective steps will be described in detail.

[(1) Step A: Coating Step]

Step A (coating step) is a step of applying a denture base coating composition on a denture base and thereby obtaining a denture base coating composition layer. The forms of the denture base and the denture base coating composition are as explained above.

The method for applying the denture base coating composition is not particularly limited; however, examples include application using a brush and/or a paintbrush; dip coating; spin coating; and spray coating. Among them, from the viewpoint that a special mechanical apparatus for coating is not needed, and from the viewpoint that even a small amount of a denture base coating composition can be applied efficiently, application using a brush and/or a paintbrush is preferred.

The coating step may further include a drying step, if necessary. The drying step is a step of drying the denture base coating composition applied on the denture base. A solvent included in the denture base coating composition layer can be volatilized by the drying step.

The method of drying is not particularly limited. The drying temperature is not particularly limited; however, generally, the drying temperature is preferably −20° C. to 150° C., more preferably 0° C. to 120° C., and even more preferably 10° C. to 90° C. The drying time is not particularly limited; however, generally, the drying time is preferably 1 second to 1 week, more preferably 5 seconds to 3 days, and even more preferably 10 seconds to 1 day. In regard to the drying step, the denture base coating composition may be dried by blowing air to the composition.

[(2) Step B: Curing Step]

Step B (curing step) is a step of applying energy to the denture base coating composition layer, thereby curing the denture base coating composition layer, and obtaining a coating film.

The method for applying energy to the denture base coating composition layer is not particularly limited; however, examples include heating and/or light irradiation.

The heating conditions are not particularly limited and are selected as appropriate based on the components included in the denture base coating composition. The heating temperature is not particularly limited; however, the heating temperature is preferably 30° C. to 150° C., more preferably 40° C. to 120° C., and even more preferably 50° C. to 100° C. The heating time is preferably 1 second to 1 week, more preferably 5 seconds to 3 days, and even more preferably 10 seconds to 1 day. The heating method is not particularly limited: however, known heating methods of using an oven, a hot plate, and the like may be used.

The conditions for light irradiation are not particularly limited and are selected as appropriate based on the components included in the denture base coating composition. The irradiation energy is not particularly limited; however, generally, the amount of irradiation is preferably 0.01 to 100) J/$cm^2$, more preferably 0.1 to 20 J/$cm^2$, and even more preferably 0.5 to 10 J/$cm^2$. The irradiation time is preferably 0.1 to 1,000 seconds, more preferably 0.5 to 500 seconds, and even more preferably 1 to 100 seconds. Examples of the light for light irradiation include ultraviolet radiation, visible light (including visible light at a particular wavelength only, such as blue wavelength), and X-radiation. Regarding the method of light irradiation, for example, a method of radiating light using a low-pressure mercury lamp, a medium-pressure mercury lamp, a high-pressure mercury lamp, a metal halide lamp, an ultraviolet lamp, a LED (light emitting diode) lamp (particularly, a blue LED lamp having light emission between 370 nm to 500 nm, or the like), a xenon lamp, a chemical lamp, a carbon arc, and the like may be used.

Meanwhile, heating and light irradiation may be carried out alone, or the two may be carried out together. In a case in which heating and light irradiation are carried out, the processes may be carried out simultaneously or may be sequentially carried out one by one.

[Other Steps]

The method for producing a coating film-bearing denture base according to the embodiments of the invention may include another step to the extent that the effects of the invention are provided. Examples of the other step include step S of surface-treating the denture base.

<Step S>

Step S is a step of surface-treating a denture base. It is preferable that the method for producing a coating film-bearing denture base according to the embodiments of the invention has step S before step A.

A coating film-bearing denture base produced by the above-described production method including the pre-step S has excellent interlayer adhesiveness between the denture base and the coating film.

The method for the surface treatment is not particularly limited, and any known surface treatment method can be used. Examples of the known surface treatment method include a sand blast method, a method of polishing with a polishing paper, a method of roughening the surface by a treating agent method or the like, a method of applying an alkali solution on a denture base and then washing the denture base with water; a corona discharge treatment; a plasma treatment; and a flame treatment.

Among them, from the viewpoint that a coating film-bearing denture base exhibiting superior effects of the invention is obtained, it is preferable that the surface treatment is carried out by a method of bringing a denture base into contact with a surface treating agent. The method of bringing the surface of a denture base into contact with a surface treating agent is not particularly limited; however, examples include a method of immersing a denture base in a surface treating agent, a method of applying a surface treating agent on a denture base, and a method of spraying a surface treating agent onto a denture base.

It is preferable that the surface treating agent includes an organic solvent. The organic solvent included in the surface treating agent is not particularly limited; however, examples include a halogen-based solvent, a ketone-based solvent, an alcohol-based solvent, an ether-based solvent, and an ester-based solvent.

The content of the organic solvent in the surface treating agent is not particularly limited; however, the content is preferably 20% to 100% by mass with respect to the total mass of the organic solvent.

Regarding the organic solvent, one kind thereof may be used alone, or two or more kinds thereof may be used in combination. In a case in which two or more kinds of organic solvents are used in combination, it is preferable that the total content is within the range described above.

In a case in which a denture base is surface-treated using a surface treating agent including an organic solvent, concavities and convexities are more easily formed on the surface of the denture base, and superior interlayer adhesiveness between the denture base and the coating film is obtained.

Above all, from the viewpoint that concavities and convexities that will be described below are formed on the surface of a denture base, it is preferable that a main component of the organic solvent included in the surface treating agent is at least one selected from the group consisting of a ketone-based solvent, an alcohol-based solvent, an ether-based solvent, and an ester-based solvent; and it is more preferably the main component is at least one selected from the group consisting of acetone and methyl ethyl ketone.

The arithmetic mean roughness Ra of the surface on the coating film side of the denture base in a coating film-bearing denture base obtainable by the above-described production method is not particularly limited; however, generally, the arithmetic mean roughness Ra is preferably 10 to 1,200 nm, more preferably 30 nm to 1,000 nm, even more preferably 50 nm to 800 nm, and particularly preferably 100 nm to 500 nm.

Meanwhile, the arithmetic mean roughness Ra can be measured by making an observation of the surface of a surface-treated denture base before being provided with a coating film, by a contact needle method and a non-contact type interference microscope.

The denture base coating composition can form a strong coating film, and the coating film has excellent performance to inhibit bacterial attachment. Therefore, the denture base coating composition may be used for use application other than those that have been previously described. Regarding the use applications, for example, a dental material that is required to have excellent performance to inhibit bacterial attachment may be mentioned. Examples of such a dental material include an adhesive material (bonding material), a primer material, a resin material (also including a composite resin and a resin cement), and coating material for uses other than denture base use (artificial teeth, natural teeth, a resin material, and the like).

A coating film obtainable by curing the above-described denture base coating composition has excellent scratch resistance and an excellent ability to inhibit bacterial attachment. Furthermore, the coating film obtainable by curing the denture base coating composition is a strong crosslinked film and also has excellent resistance to coloration and excellent resistance to thermal cycling. Meanwhile, the resistance to coloration implies a property by which the color tone of the coating film is not likely to be changed by repeatedly eating and drinking coloring foods for eating and drinking in daily life (for example, black tea, green tea, coffee, red wine, and curry). Furthermore, the resistance to thermal cycling implies a property by which the physical properties of the coating film, such as adhesiveness and abrasion resistance, are not likely to be changed before and after a thermal cycling test with respect to a temperature change inside the oral cavity caused by eating and drinking in daily life.

EXAMPLES

Hereinafter, the present invention will be described in more detail based on Examples. The materials, amounts of use, proportions, contents of treatment, procedures, and the like shown in the following Examples can be modified as appropriate, as long as the gist of the invention is maintained. Therefore, the scope of the invention is not intended to be construed limitedly by the following Examples.

Test Example 1

In order to verify the scratch resistance and the ability to inhibit bacterial attachment exhibited by a coating film obtainable using a denture base coating composition, a test was carried out by the following procedure.

Synthesis of Compound 1

In a 1-L three-neck flask equipped with a stirring blade and a cooling pipe, dimethylaminopropyl methacrylamide (manufactured by Wako Pure Chemical Industries, Ltd., 119.18 g), acetonitrile (manufactured by Wako Pure Chemical Industries, Ltd., 350 g), and p-methoxyphenol (manufactured by Wako Pure Chemical Industries. Ltd., 0.060 g) were introduced, and thus a mixed liquid was obtained. Next, while the mixed liquid was stirred, 95.32 g of 1,4-butanesultone (manufactured by Wako Pure Chemical Industries, Ltd.) was added dropwise to the mixed liquid for 30 minutes, and thereby a reaction liquid was obtained. Next, the reaction liquid was caused to react by heating for 5 hours at 80° C. Next, the reaction liquid in which the reaction had been completed was left to stand for 10 hours at room temperature, and then a white solid was precipitated out from the lower phase of the reaction liquid that had been separated into two phases. Next, the white solid was collected using a suction filtration method in a nitrogen atmosphere. The solid thus collected was stirred in 800 mL of acetone and washed. Next, after the washing was completed, the white solid that had been washed was collected again using a suction filtration method. The white solid thus collected was dried, and thus Compound 1 (192.15 g) was obtained. Compound 1 is a compound represented by Formula (1-1) described above.

Synthesis of Compound 2

Compound 2 was synthesized by using diethylene glycol bis(3-aminopropyl) ether as a raw material amine and by referring to the reaction conditions for acylation as described in JP2012-206992A. Meanwhile, Compound 2 is a compound represented by Formula (2-1) described above.

[Production of Denture Base Coating Composition]

The various compounds described above and IRGACURE 2959 (trade name, manufactured by BASF SE, described in Table 1 as "Irg-2959") were mixed at the compositions described in Table 1, and denture base coating compositions of Examples 1 to 4 were produced. IRGACURE 2959 corresponds to a photopolymerization initiator, and corresponds to a hydroxyalkylphenone compound.

Furthermore, a denture base coating composition of Example 5 was produced in the same manner as in Example 4 except that Compound 1 of Example 4 was replaced with 2-methaciyloyloxyethylphosphorylcholine (in Table 2 and Table 3, described as "MPC").

A denture base coating composition of Example 6 was produced in the same manner as in Example 2, except that Compound 1 of Example 2 was replaced with [3-(methacryloylamino)propyl]dimethyl(3-sulfopropyl)ammonium hydroxide internal salt (in Table 2 and Table 3, described as "SPBM"; corresponds to a compound represented by Formula (1-2)).

A denture base coating composition of Example 7 was produced in the same manner as in Example 3, except that Compound 1 of Example 3 was replaced with SPBM.

Meanwhile, the values shown in Table 2 and Table 3 represent the contents (mass %) of the various components with respect to the total solid content of the denture base coating composition. Furthermore, the solid content of each denture base coating composition was adjusted to be 20% by mass with methanol. The symbol "-" in Table 2 and Table 3 implies that the component was not used.

[Test on Ability to Inhibit Bacterial Attachment]

First, the surface of a polyethylene terephthalate (PET, product name "A4300", manufactured by Toyobo Co., Ltd.) film was subjected to an oxygen plasma treatment ($O_2$; 100 ml/min, for 600 seconds). Next, each of the denture base coating composition was applied on the PET film using a bar coater to a thickness that would be 1 μm as a dried film thickness, and thus a denture base coating composition layer was obtained. Next, the denture base coating composition layer-bearing PET film was placed in a drying oven at 50° C. and was dried for 5 minutes. Next, the dried denture base coating composition layer was exposed (irradiated with ultraviolet radiation) using an "ECS-401G (trade name)" UV (ultraviolet) exposure machine (light source was a high-pressure mercury lamp) manufactured by Eye Graphics Co., Ltd., at an exposure amount of 4 J/cm$^2$ (irradiation time was 5 seconds). Thus, the denture base coating composition layer was cured, and a coating film was obtained.

Next, the PET film including the coating film obtained as described above was cut out into a predetermined size, and a disc-shaped sample was produced. Furthermore, a PET film (blank) that did not include a coating film was also prepared as Comparative Example 1, and this was supplied to the test. As Comparative Example 2, a coating film was obtained in the same manner as in Example 1 except that a copolymer of MPC and a methacrylic acid ester (LIPIDURE-CM5206 manufactured by NOF Corporation; in Table 2 and Table 3, described as "Lipidure") was used, and an exposure step was not carried out. This coating film was supplied to the test.

Next, the various samples were placed on a 24-well plate. In each well, yeast form cell bodies of *C. albicans* (JCM2085, JCM is an abbreviation of Japan Collection of Microorganisms) were inoculated into YPD (yeast extract peptone dextrose) medium, and 1 mL each of a test liquid adjusted to a concentration of $10^4$ cells/mL was introduced.

Next, the 24-well plate containing the samples and the test liquid was cultured under aerobic conditions at 37° C. for 24 hours. Next, the samples after culturing were washed with a PBS (phosphate buffered saline) buffer solution, and then the numbers of bacterial cells attached to the coating composition and the PET film were quantitatively determined by a colorimetric determination method (XTT method, XTT is an abbreviation for 2,3-Bis-(2-Methoxy-4-Nitro-5-Sulfophenyl)-2H-Tetrazolium-5-Carboxanilide). The light absorbance of a PET film that did not include a coating film was taken as a reference, and the difference (amount of reduction in the light absorbance) between the light absorbance of the PET film and the light absorbance of each of the samples was determined and evaluated according to the following standards. Thus, the difference is shown in column "Bacterial attachability" in Table 2 and Table 3.

Evaluation Standards

A: The difference between the sample and the reference was 0.6 or more.

B: The difference between the sample and the reference was 0.5 or more and less than 0.6.

C: The difference between the sample and the reference was 0.4 or more and less than 0.5.

D: The difference between the sample and the reference was 0.3 or more and less than 0.4.

E: The difference between the sample and the reference was less than 0.3.

[Scratch Resistance Test]

A PET film including a coating film was produced in the same manner as in the case of the test on the ability to inhibit bacterial attachment. Also, for Comparative Example 1, a PET film including a coating film was similarly prepared.

Next, each of the samples was brushed for 60 seconds using a toothbrush wear testing machine and a toothbrush ("BETWEEN LION (trade name)", hardness was "moderate") under the conditions of a sliding speed of 126 times/min, a load of 185 g, and a stroke width of 5 mm.

The amount of wear of each of the samples after brushing was measured with a three-dimensional microprofile measurement apparatus. The results were evaluated according to the following standards, and the results are shown in Table 2 and Table 3.

A: The amount of wear was less than 0.01 μm.

B: The amount of wear was 0.01 μm or more and less than 0.1 μm.

C: The amount of wear was 0.1 μm or more.

TABLE 2

| | | Example 1 | Example 2 | Example 3 | Example 4 |
|---|---|---|---|---|---|
| Denture base coating composition | Compound 1 | — | 97 | 48.5 | 29.1 |
| | Compound 2 | 97 | — | 48.5 | 67.9 |
| | MPC | — | — | — | — |
| | SPBM | — | — | — | — |
| | Lipidure | — | — | — | — |
| | Irg-2959 | 3 | 3 | 3 | 3 |
| Evaluation | Bacterial attachability | C | B | B | A |
| | Scratch resistance | A | B | A | A |

TABLE 3

| | | Example 5 | Example 6 | Example 7 | Comparative Example 1 | Comparative Example 2 |
|---|---|---|---|---|---|---|
| Denture base coating composition | Compound 1 | — | — | — | — | — |
| | Compound 2 | 67.9 | — | 48.5 | — | — |
| | MPC | 29.1 | — | — | — | — |
| | SPBM | — | 97 | 48.5 | — | — |
| | Lipidure | — | — | — | — | 100 |
| | Irg-2959 | 3 | 3 | 3 | — | — |
| Evaluation | Bacterial attachability | C | B | B | E | D |
| | Scratch resistance | B | B | A | C | C |

From the results shown in Table 2 and Table 3, it was found that coating films obtainable by the above-described coating compositions have an excellent ability to inhibit bacterial attachment and excellent scratch resistance. On the other hand, in Comparative Example 1 that did not include a coating film, the effects of the invention were not obtained in both the ability to inhibit bacterial attachment and scratch resistance. Furthermore, with a coating film formed using the coating composition of Comparative Example 2 that did not include both Compound 1 (corresponding to the first compound) and Compound 2 (corresponding to the second compound), the effects of the invention were not obtained.

Furthermore, coating films obtained from the coating compositions of Example 3 and Example 4 that included Compound 1 and Compound 2 had a superior ability to inhibit bacterial attachment compared to the coating film obtained from the coating composition of Example 1. Furthermore, those coating films had superior scratch resistance compared to the coating film obtained from the coating composition of Example 2.

Coating films formed using the coating compositions of Examples 1 to 4 in which the monomers and polymers included in the coating compositions comprise at least one selected from the group consisting of the first compound and the second compound, had a superior ability to inhibit bacterial attachment and/or superior scratch resistance compared to Example 5.

Furthermore, a coating film obtainable from the coating composition of Example 6 that included a compound represented by Formula (1-2) had a performance equivalent to that of the coating film obtainable from the coating composition of Example 2.

Test Example 2

Next, a test was carried out by the following procedure in order to verify the influence of a surface treatment of a denture base on the adhesiveness between a coating film and the denture base.

Example 2-1

A plate-shaped body that measured 3 cm on each side and had a thickness of 5 mm was obtained using an acrylic resin for denture base (ISORESIN H. Denken-Highdental Co., Ltd.) by a wet heating polymerization method that is conventionally carried out. Next, the plate-shaped body was polished with a polishing paper #400 and was further polished with a polishing paper #8000, and thereby a denture base for test was obtained. At this time, the arithmetic mean roughness Ra of the surface of the denture base was about 10 nm.

<Surface Treatment>

Next, the denture base thus obtained was immersed in dichloromethane (100% by mass) for one minute, and then the denture base was taken out and dried. Thereby, a surface-treated denture base was obtained. At this time, the arithmetic mean roughness of the surface of the surface-treated denture base was 1,000 nm. Meanwhile, the arithmetic mean roughness (Ra) was measured with a non-contact type interference microscope.

<Formation of Coating Film>

Net, a denture base coating composition described in Table 4 was applied on this surface-treated denture base so as to obtain a thickness of the cured film of 3 μm, and thus a denture base coating composition layer was obtained. Next, the denture base coating composition layer-bearing surface-treated denture base was placed in a drying oven at 50° C. and was dried for 5 minutes.

Next, the dried denture base coating composition layer was exposed using an "ECS-401G (trade name)" UV (ultraviolet) exposure machine (light source was a high-pressure mercury lamp) manufactured by Eye Graphics Co., Ltd. at an exposure amount of 4 $J/cm^2$, and the denture base coating composition layer was cured. Thus, a coating film-bearing denture base was obtained.

Example 2-2 to Example 2-8 and Example 2-10

Coating film-bearing denture bases were obtained in the same manner as in Example 2-1, except that the surface treating agent was replaced with dichloromethane, the organic solvents described in Table 4 were used, and the denture base coating compositions described in Table 4 were used. The respective arithmetic mean roughnesses of the surface on the coating film side of the coating film-bearing denture bases were as described in Table 4.

Example 2-9

A coating film-bearing denture base was obtained by a method similar to that described in Example 2-1, except that a surface treatment using a surface treating agent was not carried out. The arithmetic mean roughness of the coating film-bearing denture base obtained as described above was 10 nm (in Table 4, the "denture base after surface treatment" and "arithmetic mean roughness Ra" are described; however, in Example 2-9, a surface treatment was not carried out).

(Scratch Resistance Test)

For the coating film-bearing denture bases of Example 2-1 to Example 2-10 obtained as described above, scratch resistance was measured by a method similar to that of Test Example 1. As a result, the amounts of wear of the coating film-bearing denture bases of Example 2-1 to Example 2-10 were less than 0.1 μm, which were within the range of practical use.

(Test on Performance to Inhibit Bacterial Attachment)

Each of the coating film-bearing denture bases was cut into a size of 1 cm on each side, and the specimen was placed on a 24-well plate. On each well, yeast type cell bodies of *C. albicans* (JCM2085, JCM is an abbreviation of Japan Collection of Microorganisms) were inoculated into YPD (yeast extract peptone dextrose) medium, and 1 mL each of a test liquid adjusted to a concentration of 970 cells/mL was introduced.

Next, the 24-well plate containing the specimen and the test liquid was cultured under aerobic conditions at 37° C. for 36 hours. Next, the specimen after culturing was washed with a PBS (phosphate buffered saline) buffer solution, and then the number of bacterial cells attached to the specimen was quantitatively determined by a colorimetric determination method (XTT method, XTT is an abbreviation for 2,3-Bis-(2-Methoxy-4-Nitro-5-Sulfophenyl)-2H-Tetrazolium-5-Carboxanilide). The light absorbance of a denture base (Ra was about 10 nm) that did not include a coating film was taken as a reference, and the difference (amount of reduction in the light absorbance) between the light absorbance of the denture base and the light absorbance of each of the coating film-bearing denture bases was determined and evaluated according to the following standards. Thus, the difference is shown in column "Performance to inhibit bacterial attachment" in Table 4.

A: The difference between the sample and the reference was 0.6 or more.

B: The difference between the sample and the reference was 0.5 or more and less than 0.6.

C: The difference between the sample and the reference was 0.4 or more and less than 0.5.

(Evaluation of Adhesiveness)

Each of the coating film-bearing denture bases was subjected to a thermal cycling test of immersing in ion-exchanged water and repeating an operation of shuttling between constant temperature tanks at 4° C. and 60° C. for 30 seconds for 3,000 times, and the adhesiveness was evaluated from the area of the coating film remaining on the denture base. The area of the remaining coating film with respect to the surface area of the denture base was expressed in percentage as a coating film ratio, and the coating film ratio was evaluated according to the following standards. The results are shown in Table 4.

A: The coating film ratio was 90% or more.

B: The coating film ratio was 70% or more and less than 90%.

C: The coating film ratio was 50% or more and less than 70%.

D: The coating film ratio was less than 50%.

TABLE 4

| | Surface treatment of denture base | | | Denture base coating composition | | | Evaluation | |
|---|---|---|---|---|---|---|---|---|
| | Presence or absence of surface treatment | Main component of surface treating agent (organic solvent) | Denture base after surface treatment Arithmetic mean roughness Ra (nm) | Particular compound Compound 1 | Particular compound Compound 2 | Polymerization initiator Irg2959 | Adhesiveness | Performance to inhibit bacterial attachment |
| Example 2-1 | Present | Dichloromethane | 1000 | 97 | — | 3 | C | B |
| Example 2-2 | Present | Tetrahydrofuran | 800 | 97 | — | 3 | B | B |
| Example 2-3 | Present | Acetone | 350 | 97 | — | 3 | A | B |
| Example 2-4 | Present | Methyl ethyl ketone | 300 | 97 | — | 3 | A | B |
| Example 2-5 | Present | Ethyl acetate | 50 | 97 | — | 3 | B | B |
| Example 2-6 | Present | 2-Propanol | 30 | 97 | — | 3 | C | B |
| Example 2-7 | Present | Acetone | 350 | 92 | 5 | 3 | A | A |
| Example 2-8 | Present | Methyl ethyl ketone | 300 | 92 | 5 | 3 | A | A |
| Example 2-9 | None | — | 10 | 97 | — | 3 | D | C |
| Example 2-10 | Present | 2,2,2-Trifluoroethanol | 1100 | 97 | — | 3 | D | C |

As described in Table 4, the coating film-bearing denture base of Example 2-7, which had an arithmetic mean roughness Ra of the surface on the coating film side of the denture base was 30 to 1,000 nm, had superior adhesiveness and superior performance to inhibit bacterial attachment, compared to the coating film-bearing denture bases of Example 2-9 and Example 2-10.

Furthermore, the coating film-bearing denture base of Example 2-7 that used a surface-treated denture base had superior adhesiveness and superior performance to inhibit bacterial attachment, compared to the coating film-bearing denture base of Example 2-9.

The coating film-bearing denture base of Example 2-7, in which the surface treating agent was at least one selected from the group consisting of acetone and methyl ethyl ketone, had superior adhesiveness and superior performance to inhibit bacterial attachment, compared to the coating film-bearing denture bases of Example 2-5 and Example 2-6.

What is claimed is:

1. A denture base coating composition comprising a first compound represented by Formula (1-0) and a second compound represented by Formula (2-0), wherein the content mass ratio of the content of the first compound to the content of the second compound in the denture base coating composition is 10/90 to 90/10, (1-0)

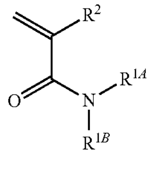

in Formula (1-0), $R^{1A}$ and $R^{1B}$ each independently represents a group represented by Formula (1A) or a hydrogen atom, at least one selected from the group consisting of $R^{1A}$ and $R^{1B}$ is a group represented by Formula (1A), and $R^2$ represents a hydrogen atom or a methyl group, (1A)

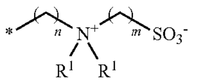

in Formula (1A), $R^1$'s each independently represent a methyl group, an ethyl group, an n-propyl group, or an i-propyl group, m represents an integer from 1 to 4, n represents an integer from 2 to 4, a plurality of $R^1$'s may be identical with or different from one another, and the symbol * represents a position of bonding to the nitrogen atom in Formula (1-0), and (2-0)

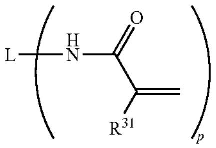

in Formula (2-0), $R^{31}$ represents a hydrogen atom or a methyl group, p represents an integer from 2 to 4, L represents a p-valent linking group, and a plurality of $R^{31}$'s may be identical with or different from one another.

2. The denture base coating composition according to claim 1, wherein the second compound is at least one selected from the group consisting of a compound represented by Formula (2-01) and a compound represented by Formula (2-02), (2-01)

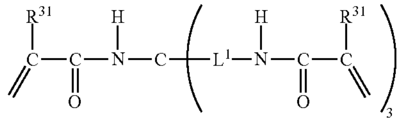

(2-02)

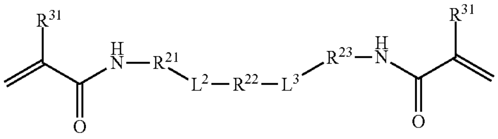

(III)

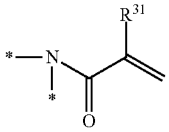

in Formula (2-01), $R^{31}$'s each independently represent a hydrogen atom or a methyl group, $L^1$'s each independently represent —O—, an alkylene group having 2 to 4 carbon atoms, or a divalent linking group combining these, in Formula (2-02), $R^{31}$'s each independently represent a hydrogen atom or a methyl group, $R^{21}$ and $R^{23}$ each independently represents —O—, an alkylene group having 1 to 4 carbon atoms, or a divalent linking group combining these, $R^{22}$ represents —O—, an alkylene group having 1 to 4 carbon atoms, a group represented by Formula (III), or a divalent linking group combining these, and $L^2$ and $L^3$ each independently represents a single bond or a group represented by Formula (III), and in Formula (III), $R^{31}$ represent a hydrogen atom or a methyl group, and the symbol * represents a position of bonding.

3. The denture base coating composition according to claim 1, wherein the first compound is a compound represented by Formula (1-01), and the second compound is a compound represented by Formula (2), (1-01)

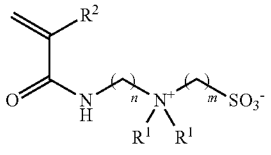

in Formula (1-01), $R^1$'s each independently represent a methyl group, an ethyl group, an n-propyl group, or an i-propyl group, $R^2$ represents a hydrogen atom or a methyl group, m represents an integer from 1 to 4, n represents an integer from 2 to 4, and a plurality of $R^1$'s may be identical with or different from one another, and (2)

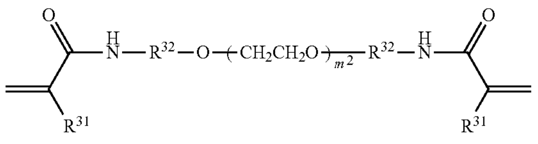

in Formula (2), $R^{31}$'s each independently represent a hydrogen atom or a methyl group, $R^{32}$'s each independently represent an ethylene group, a 1,2-propylene group, or a 1,3-propylene group, $m^2$ represents an integer from 0 to 2, and a plurality of $R^{31}$'s and a plurality of $R^{32}$'s may be identical with or different from one another.

4. The denture base coating composition according to claim 1, wherein the first compound is a compound represented by Formula (1-1) or a compound represented by Formula (1-2), and the second compound is a compound represented by Formula (2-1), (1-1)

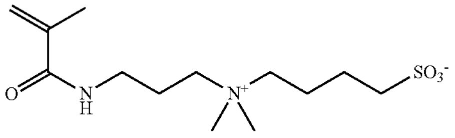

(1-2)

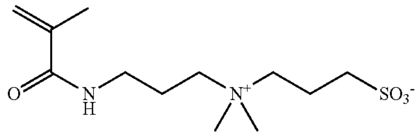

(2-1)

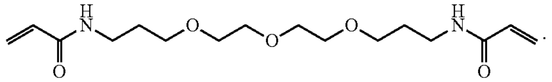

5. The denture base coating composition according to claim 1, further comprising a polymerization initiator.

6. A coating film-bearing denture base comprising a denture base and a coating film formed on the denture base, the coating film being obtained by curing the denture base coating composition according to claim 1.

7. The coating film-bearing denture base according to claim 6, wherein an arithmetic mean roughness Ra of the surface of the denture base on the coating film side is 30 to 1,000 nm.

8. The coating film-bearing denture base according to claim 6, wherein the denture base is a surface-treated denture base treated with a surface treating agent.

9. The coating film-bearing denture base according to claim 8, wherein the surface treating agent includes an organic solvent, and a main component of the organic solvent is at least one selected from the group consisting of a ketone-based solvent, an alcohol-based solvent, an ether-based solvent, and an ester-based solvent.

10. The coating film-bearing denture base according to claim 9, wherein the main component of the organic solvent is at least one selected from the group consisting of acetone and methyl ethyl ketone.

11. A plate denture comprising the coating film-bearing denture base according to claim 6.

12. A method for producing a coating film-bearing denture base comprising a denture base and a coating film formed on the denture base, the method comprising:

step A of applying the denture base coating composition according to claim 1 on the denture base and obtaining a denture base coating composition layer; and step B of applying energy to the denture base coating composition layer, thereby curing the denture base coating composition layer, and obtaining a coating film.

13. The method for producing a coating film-bearing denture base according to claim 12, the method further comprising step S of surface-treating the denture base, before the step A.

14. The method for producing a coating film-bearing denture base according to claim 13, wherein the step S is a step of bringing the surface of the denture base into contact with a surface treating agent.

15. The method for producing a coating film-bearing denture base according to claim 14, wherein the surface treating agent includes an organic solvent, and a main component of the organic solvent is at least one selected from the group consisting of a ketone-based solvent, an alcohol-based solvent, an ether-based solvent, and an ester-based solvent.

16. The method for producing a coating film-bearing denture base according to claim 15, wherein the main component of the organic solvent is at least one selected from the group consisting of acetone and methyl ethyl ketone.

17. The denture base coating composition according to claim 1, wherein the coating composition comprises, the first compound represented by Formula (1-1) or Formula (1-2), the second compound represented by Formula (2-1), and a polymerization initiator, (1-1)

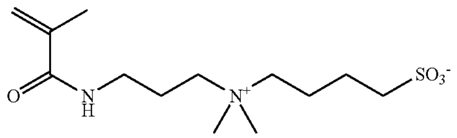

(1-2)

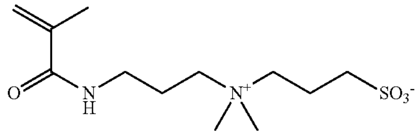

(2-1)

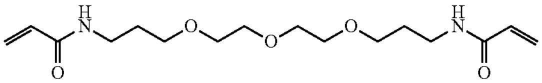

.

* * * * *